United States Patent
Sundström

[11] Patent Number: 5,147,339
[45] Date of Patent: Sep. 15, 1992

[54] DRESSING MATERIAL FOR THE TREATMENT OF WOUNDS, AND CORPUSCLES FOR USE IN THE PRODUCTION THEREOF

[75] Inventor: Staffan Sundström, Helsingborg, Sweden

[73] Assignee: Coloplast A/S, Denmark

[21] Appl. No.: 375,019

[22] PCT Filed: Sep. 19, 1998

[86] PCT No.: PCT/DK88/00153
§ 371 Date: May 31, 1989
§ 102(e) Date: May 31, 1989

[87] PCT Pub. No.: WO89/02754
PCT Pub. Date: Apr. 6, 1989

[30] Foreign Application Priority Data
Sep. 22, 1987 [DK] Denmark ............... 4962/87

[51] Int. Cl.⁵ .............................. A61F 13/02
[52] U.S. Cl. ..................... 604/307; 604/304; 424/447; 523/111; 602/56
[58] Field of Search ........... 604/304, 307, 890.1; 424/44, 447, 448; 523/111; 602/56

[56] References Cited
U.S. PATENT DOCUMENTS

| | | |
|---|---|---|
| 3,742,951 | 7/1973 | Zaffaroni ............ 604/304 |
| 4,538,603 | 9/1985 | Pawelchak et al. ...... 128/156 |
| 4,624,665 | 11/1986 | Nuwayser ............ 604/307 |
| 4,699,792 | 10/1987 | Nick et al. ............ 604/307 |
| 4,704,119 | 11/1987 | Shaw et al. ............ 604/304 |

FOREIGN PATENT DOCUMENTS 0369080  4/1925  Fed. Rep. of Germany ........ 424/44

Primary Examiner—Randall L. Green
Assistant Examiner—Paul Prebilic
Attorney, Agent, or Firm—Ostrolenk, Faber, Gerb & Soffen

[57] ABSTRACT

A dressing material for the treatment of wounds comprises a dressing and corpuscles which are placed on or may be placed on the dressing, most frequently by means of an irreversible adhesive connection, and which contains at least one substance which is active in wound care. The corpuscles consist of a solid, continuous, hydrophobic, biologically inert, water-insoluble matrix which is stable at temperatures below 50°C. and which contains at least one hydrophilic, discontinuous phase in which one or more biologically active substances are dispersed, dissolved or are present as a coating thereon. As active substances may for example be used EGF (epidermal growth factor) EGF-urogastron, immunoglobulines, antiseptics, antibiotics, antiinflammatory agents, proteolytics and local anaesthetics, heparin and vasodilators.

12 Claims, 1 Drawing Sheet

DRESSING MATERIAL FOR THE TREATMENT OF WOUNDS, AND CORPUSCLES FOR USE IN THE PRODUCTION THEREOF

FIELD OF THE INVENTION

The present invention relates to a dressing material for the treatment of wounds in the surface, oral cavity or other accessible mucous membranes of the human body by successive release of at least one substance which is biologically active in wound care and which is discontinuously present in a solid, hydrophobic, water-insoluble, biologically inert, continuous matrix which is stable at temperatures below 50° C. and which forms part of one or more small bodies or corpuscles connected to a bandage intended to be attached to the skin around the wound, preferably by adhesion.

BACKGROUND OF THE INVENTION AND PRIOR ART

A range of bandages are known which are adhesive on the side facing the skin or the wound, especially adhesive plasters, and — most important in the present context — in the form of skin barriers having a continuous phase of a skin-friendly, adhesive material preferably comprising an elastomer such as a styrene-olefine-styrene block copolymer, a natural rubber or silicone rubber. The adhesive material may be polymers and copolymers of dicyclopentadiene or pinene, or it may be polyisobutylene or similar substances. According to known technique one or more hydrocolloids may be present as a separate disperse phase. Examples of patent specifications describing this technique are U.S. Pat. No. 3,339,546, U.S. Pat. No. 4,231,369 and U.S. Pat. No. 4,367,732. At least the skin barriers known from the two latter specifications are liquid-absorbing.

In the skin and wound treatment it is known to incorporate biologically active substances, for instance antibiotics and antiseptics, in the continuous phase of such adhesive bandages, cf. e.g. EP patent specification No. 55,023 which recommends the incorporation of antiseptics in order to protect the bandage itself; U.S. Pat. No. 4,307,717; DK patent specification No. 109,225, cf. especially Examples 7-9; U.S. Pat. Nos. 4,231,369 and 4,367,732 referred to above; and the U.S. Pat. Nos. 370,893 of Apr. 22, 1982 and 507,657 of Jun. 27, 1983. European patent publication No. 272,149 suggests incorporating a biologically active substance in a separate phase which is dispersed in the continuous phase, thereby obtaining a liquid-dependent release of the active substance, whereas the active substance is released substantially independently of liquid from the bandages in which it is present in the continuous phase.

From various patent specifications, i.a. EP publication No. 63,604, PCT publication No. WO82/00099 and U.S. Pat. No. 3,769,071 it is known to cut sheets of bandages, having incorporated therein a biologically active material, into corpuscles which are placed on the patient on the site of treatment.

From U.S. Pat. No. 4,597,960 an astringent hemostatic preparation is known which is provided with a granulated hemostatic (an inorganic aluminium or ferric salt) encapsulated in a cellulose-based, biocompatible polymer which is soluble in body fluids. The granulated hemostatic itself may be particles which are attached to an adhesive layer on an absorbing pad, for instance made from gauze or a foam material, and these elements together may form corpuscles which are attached to the adhesive surface of a conventional bandage provided with an adhesive layer. The side of the granulated hemostatic facing the skin may optionally be covered with a further layer of an adhesive which on the side facing the skin is provided with a further absorbing pad of the same kind as that mentioned above. The hemostatic effect will occur when the capsule-forming polymer is dissolved by the body fluids whereby no substantial delay nor protracted effect of the aluminium or ferric salts will occur.

EP patent specification No. 170,010 describes a self-adhesive plaster comprising approximately spherical cap-shaped segments containing one or more biologically active substances arranged on a carrier for transdermal administration and, in order to exert an adhesive effect on the biologically active substance, also comprising approximately spherical cap-shaped adhesive segments spatially separated from the active substance segments and comprising adhesive systems which can be processed as a dispersion, plastisol or organosol. The micro-structure of the biologically active segments has not been explained, but according to the Example of the specification they consist of a thickened organic solution of the active substance. The plaster is manufactured by applying the respective segments by means of a screen printer. The active segments are cut from a sheet of segment material by means of a sieve cylinder. The way of manufacture makes it difficult to provide the plaster with active segments of different composition, including concentration.

GB No. 2,184,019 A describes a transdermal or dermal patch in which an active substance has been embedded in a number of compartments which are enclosed between a backing layer, which is impermeable to the active substance, and a membranous layer, through which it is able to penetrate. The active substance is present in the compartments as a dispersion or solution in a more or less low-viscosity fluid or an ointment-like substance. The specification emphasizes that the carrier fluid may be more liquid than that used in known plasters comprising only one compartment instead of a number of compartments. It is, however, said that the compartments may be 30 cm$^2$, but preferably not more than 20 or 13.3 cm$^2$. Compartments that large will not allow a very precise control of the delivery rate of the active substance, for instance to vary it within a very few cm.

It is the object of the invention to provide a dressing material of the kind stated in the opening paragraph, which differs from the known technique by being suitable for a very varied, individual wound treatment which can be adapted very precisely to the site of treatment and which due to the structure thereof releases the biologically active substance or substances slowly by virtue of penetration of wound exudate through the matrix.

SUMMARY OF THE INVENTION

This is attained by the present dressing material which according to the invention is characterized in that at least one hydrophilic discontinuous phase is present in the continuous matrix and that the biologically active substance or substances is/are dispersed or dissolved in at least one such discontinuous hydrophilic phase or present as a coating thereon.

Modern therapy shows a marked tendency towards a more and more sophisticated skin and wound treatment, even by using substances which are only rarely used in such treatments and which cannot in practice be incorporated into standard dressings.

The present dressing material might be available ready for use, viz. as a dressing with corpuscles attached thereto, but the main object of the invention aims at providing them separately, optionally in packages containing both dressing and corpuscles so that the nursing staff or perhaps the patient himself just before use places a desired number of corpuscles in a desired configuration on the dressing.

The invention, therefore, also relates to corpuscles to be adhesively placed on the side of a dressing intended to face the skin of the patient, said corpuscles consisting of a solid, hydrophobic, water-insoluble, biologically inert, continuous matrix which is stable (i.e., does not decompose, melt or dissolve) below 50° C. and which contains one or more discontinuous phases including at least one phase containing at least one substance which is biologically active in wound care, and according to the invention such corpuscles are characterized in that the biologically active substance or substances is/are dissolved or dispersed in at least one hydrophilic phase discontinuously present in the matrix or present as a coating thereon.

DETAILED EXPLANATION OF THE INVENTION

The dressing itself may be either adhesive or non-adhesive, or parts of it may be adhesive and other parts may be non-adhesive. If the dressing in its entirety is non-adhesive, it is attached to the patient by means of a conventional sticking plaster or by means of a tape-formed dressing such as a gauze bandage. Appropriately it may on the side facing the corpuscles wholly or partly consist of a skin care substance of the kinds known from e.g. the U.S. Pat. Nos. 3,339,546, 4,231,369 or 4,367,732 mentioned hereinbefore. On the opposite side the dressing may be provided with a protective cover, which is to be removed just before use, or with a textile material usually used in skin and wound care.

In some cases even a skin-friendly dressing as the one mentioned here or generally speaking adhesive substances should not get into touch with the wound to be treated, e.g. in case of a major abrasion or a burn, and in such cases the matrix and the corpuscles may according to the invention be non-adhesive on the side intended to face the wound. The side of separate corpuscles intended to face a dressing may then for instance be provided with a pressure-sensitive adhesive agent, an adhesive skin barrier material as just mentioned or some other sealing agent in order to avoid that the adhesive dressing material between the corpuscles will get into contact with the wound.

The individual corpuscles may have any shape, e.g. be circular, oval or angular, especially square, and they may have any appropriate size, e.g. from 5 mm$^2$ to 5 cm$^2$, measured in the surface dimension of the dressing. Their thickness may vary, expediently between 0.1 and 2 mm. Most appropriately the individual matrixes may be of constant thickness, but may also be arched, deposited e.g. as drops of a molten material. They may be placed or have been positioned on the dressing in an arbitrary pattern, e.g. that of a lattice or circle the outer circumference of which corresponds as closely as possible to the wound to be treated. In some cases only one such corpuscle should be placed on the dressing, e.g. in case of very small wounds.

The matrix, which may be considered a structure-forming element or a structure-phase in the corpuscles, does not normally contain any biologically active substance as part of the continuous phase; and if it does, it is of another kind than the substance or substances intended for wound care. It may consist of any hydrophobic, flexible, biologically harmless including non-allergenic material which is usable in dressings and does not decompose, melt or dissolve at temperatures below 50° C., and into which discontinuous hydrophilic and possibly also discontinuous hydrophobic phases of another nature than that of the matrix may be incorporated. As examples may be mentioned various polymers such as styrene-butadiene and styrene-isoprene blockcopolymers, silicone rubbers, ethylene-propylene rubbers, hydrophobic polyacrylate and metacrylate esters and polyurethanes, each comprising suitable emollients where necessary.

The discontinuous phase or any discontinuous phase may be incorporated into the material forming the matrix by a suitable liquefaction of the matrix material and incorporation of the discontinuous phases by means of, e.g., the normal emulsification or dispersion techniques. The emulsification may for instance consist in dissolution in an organic solvent or preferably in melting the matrix material. Especially if the discontinuous phase is a polyurethane, the admixture of it may be performed by mixing a pre-polymer with the liquefied continuous phase, after which a cross-linking of the pre-polymer will take place, e.g. by UV- or $\beta$-irradiation or by the influence of heat.

The corpuscles have to be relatively thin, and even if their matrix is hydrophobic, liquids — wound exudate — may diffuse therethrough to a certain degree so that the hydrophilic phases will get the possibility of expanding and thereby get into contact with the wound.

The discontinuous, hydrophilic phase or any such phase containing one or more substances which are biologically active in wound care, may consist of a water-soluble oligo- or polysaccharide, such as solubilized starch or cellulose or a cellulose derivative such as e.g. methyl- or ethylcellulose. The biologically active material or materials are incorporated e.g. by dissolving the phase material in water or an aqueous solution, after which the biologically active substance or substances is/are dispersed or dissolved in the solution.

The use of more than one active disperse phase may be applied to adjust the velocity at which the active substance or substances are released to the wound. Such adjustment may take place in various ways. One way is that the discontinuous phases are hydrophilic in different degrees whereby they are dissolved at uneven rate in the wound exudate. Another way is that the concentration of identical biologically active substances is different in different hydrophilic phases that are active in wound care, including those systems in which the biologically active substance is protected against bacterial decompositions in the clinical situation. Many biologically active substances usable in wound care, e.g. enzymes, are sensitive to being decomposed by, i.a. proteases which are frequently present in wound secretions, and such decomposition may be counteracted by coating the phase or phases with an antiseptic, or by the presence of the antiseptic and the enzyme in separate phases. A third way of adjustment is that different phases active in wound care, contain different biologically active substances having fundamentally similar or fundamentally dissimilar biological activities. Optionally one phase which is biologically active in wound care may contain a hemostatic - e.g. an inorganic aluminium salt or a ferric salt — in a parent material which is easily soluble in water. Thereby a rapid onset of a hemostatic effect is attained, while one or more other substances, active in wound care, will be effective over a longer period of time.

Special substances which are suited for use as a discontinuous hydrophilic phase containing a biologically active substance, are polyvinyl pyrrolidinones (povidone) such as "Kollidon" ® and methylcellulose and gelatin.

The matrix may optionally also contain biologically inactive discontinuous phases, passive disperse phases which may for instance be hydrophilic and contain one or more substances that activate or react with the active phase while it releases the biologically active substance to the wound, when the active phase like said passive phase has absorbed liquid from the wound exudate. The basic substance of each such passive phase has to differ from the basic substance of the phase or phases which are biologically active in wound care, in order not to unnecessarily impede the introduction into the matrix.

As a biologically inactive disperse phase for affecting the desintegration of the matrix one may use substances which reduce the melting point or raise the water-solubility thereof (emollients, solubilizing agents). As biologically active phases there may a.o. be used substances having a cosmetic effect, e.g. dye-stuffs or pigments, pH indicators and temperature indicators.

A hydrophilic material or a hydrophobic material which is immissible with the matrix and which has a content generating gaseous substances under the influence of the wound exudate may be present as one or more biologically passive discontinuous phases. Said content may, e.g. be a solid acid such as for instance lactic acid or citric acid and a salt of a carbonic acid which by contact with the acid will form carbon dioxide. The purpose of said phase may be to establish a foam-like structure in the matrix in order to promote a comparatively rapid release of the substance which is biologically active in wound care. Possibly the acid and the carbonic acid salt, for instance calcium carbonate or calcium bicarbonate, may be present in separate phases; if so, the basic substance of each of said phases has to be of the same kind in order to ensure that the release will take place at the same rate.

Such gases, e.g. carbon dioxide formed by bicarbonate and citric acid, may, a.o., be effective in the displacement of oxygen; it is supposed that at least certain types of wounds have to be exempted from free oxygen, and free oxygen may hamper the angionesis.

Finally there may be one or more passive disperse phases, which are hydrophilic or hydrophobic and are immiscible with the matrix and further contain substances which affect the matrix itself. They may e.g. be pH-regulators if the matrix is pH-sensitive.

As examples of biologically active substances which may suitably be applied to wounds including abrasions and burns, by means of the present dressing material, may besides the hemostatics mentioned above be mentioned antiseptics such as iodine and iodine compounds ( e.g. a complex of iodine and a 1-vinyl-2-pyrrolidone-homopolymer for the treatment of burns, silver nitrate or silver acetate), chlorohexidine, benzalkone and chloramine; antibiotics such as neomycine, amphotericine, fusidic acid and the tetracyclines; antiinflammatory agents, e.g. antiinflammatory steroids such as cortisone, hydrocortisone, betametasone and derivatives thereof, prednisone and alkylderivatives thereof, prednisolone, triamcinolone and derivatives thereof such as the acetonide, and dexametasone, or non-steroid antiinflammatory substances such as salicylic acid and derivatives thereof, especially acetylsalicylic acid; local anaesthetics such as lidocaine, bupivicaine, tetracaine, cincocaine and benzocaine salol; anabolic steroids for building up tissues under wound healing, e.g. metandienone; proteolytic agents for the decomposition of fibrine, e.g. trypsine; vasodilating substances for improving the flow of blood during wound healing, e.g. tolazoline; and heparine and other thrombosis-hampering substances.

The present dressing material is especially suited for protracted release of certain biologically active substances which affect the tissue formation and tissue stabilization. As examples may be mentioned ascorbic acid and EGF (epidermal growth factor), EGF-URo (EGF-urogastron) and especially humane EGF-URo, also known as anthelone, which stimulates the regeneration of the skin, and somatostatine, somatotropine, asellacrine, and TGF, $\alpha$ and $\beta$.

Further substances for which the dressing material and corpuscles according to the invention are especially suited are the immunoglobulines (Ig) and other globulines, e.g. lysozyme (globuline $G_1$), which is known as a mucolytic and antiviral medicament.

The corpuscles may have been placed or may be positioned on the dressing in an arbitrary suitable pattern. The distance between the individual corpuscles may be utilized to regulate the intensity of the treatment, which may also wholly or partly be regulated by the concentration of the active substance or substances in the active discontinuous phase, the concentration of the latter in the matrix and the nature of the matrix; the matrix may be made from substances which are dissolved more or less rapidly by the wound secretions and the water therein.

The side of the corpuscles facing the skin will normally be provided with a protective cover, e.g. of siliconized paper. The same applies to possible adhesive surfaces of the dressing. This applies to corpuscles and dressings whether they are supplied ready for use with the former attached to the latter or they are supplied separately.

If the corpuscles are supplied separately from the dressing, they may for instance be encapsulated in the type of blister foil packing which is well-known for the supply of various tablets.

Apart from the protective cover or cover layer, which is preferably present on both sides thereof, such separate corpuscles may simply consist of the matrix with the active discontinuous phase or phases and optionally one or more further phases. If so is the case, the separate corpuscles can only be used for attachment to a dressing provided with an area having an adhesive surface, e.g. of a skin-friendly pressure-sensitive sealing agent or one of the skin barrier materials known e.g. from the patent specifications U.S. Pat. No. 3,339,546 or DK Nos. 147,034 and 147,035.

If the corpuscles are to be used for a non-adhesive dressing or part of a dressing, they have to be provided with the layer of adhesive.

The thickness dimension shown in the Figures is not necessarily correct relative to the width/longitudinal dimension.

DETAILED DESCRIPTION OF PREFERRED EMBODIMENTS

Figure 1:
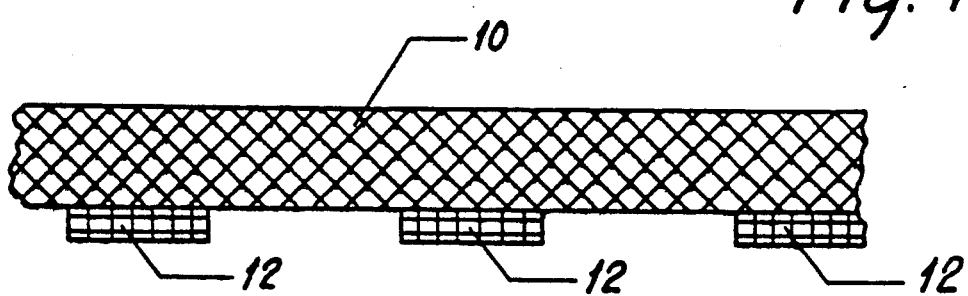
FIG. 1 shows schematically a longitudinal section of a dressing according to the invention.

In FIG. 1, 10 represents a dressing to which a number of small bodies or corpuscles have been attached.

The dressing 10 has not been structurized detailedly in the drawing because in principle it may be of any known kind, adhesive or non-adhesive, or of a non-adhesive woven or non-woven textile material which in an area may be provided with an adhesive which must be skin-friendly and which is preferably a skin barrier material of the kinds known e.g. from the U.S. Pat. Nos. 3,339,546, 4,231,369 and 4,367,732 mentioned hereinbefore. On the surface intended to be turned towards the patient the dressing in an area, optionally in its entirety, is provided with the corpuscles 12. This area of the dressing 10 may, as the surface of the dressing facing the skin, in its entirety be non-adhesive or adhesive. If it is non-adhesive the corpuscles on the side intended to face the dressing 10 must be provided with an adhesive layer, which does not necessarily have to be but preferably is skin-friendly as further explained below. The corpuscles 12 may optionally be attached to the dressing 10 by means of an irreversible adhesive connection.

Figure 2:
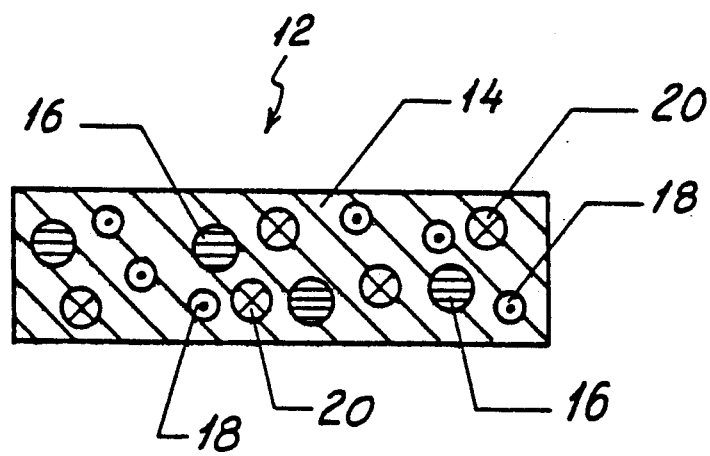
FIGS. 2-3 show schematically on a larger scale two different embodiments of corpuscles attached to or adapted to attachment to a dressing forming part of the dressing material shown in FIG. 1.
Figure 3:
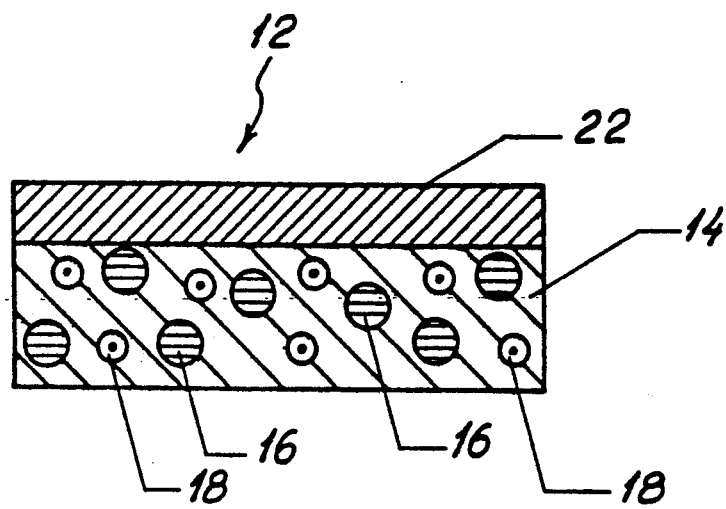

Various embodiments of the corpuscles 12 are shown in FIGS. 2-3. They may be attached to the dressing 10 by the manufacturer or may be separate and adapted to be attached thereto.

The embodiment shown in FIG. 2 is the simplest since it merely consists of a hydrophobic, preferably non-adhesive continuous matrix or phase 14 in which one or more discontinuous phases as mentioned hereinbelow are discontinuous phases.

In any case the matrix 14 contains at least one active phase 16 which is active in wound care and which contains one or more biologically active substances. The phase 16 is hydrophilic and hence insoluble in the matrix. When the wound exudate diffuses through the matrix, the biologically active substance or substances will be released and get into contact with the wound to be treated. The rate of release may be affected by regulation of the physical properties of the hydrophobic matrix, e.g. by the matrix containing hydrophilic groups to a higher or lower degree but at any rate low degree.

The matrix may also contain one or more phases 18 which are inert in the wound treatment and which contain one or more substances which when liberated will activate one or more active substances in a phase 16.

Besides, the matrix may contain one or more further discontinuous phases 20 which may be hydrophilic or hydrophobic (in that case incompatible with the matrix) and which may liberate gaseous substances, e.g. for the formation of a foam structure for gradually accelerating the release of the biologically active material.

The matrix 14 in the embodiment shown in FIG. 3 is in principle of the same kind at that shown in FIG. 2, but only the phases 16 and 18 are present. The corpuscle according to FIG. 3 differs from that shown in FIG. 2 by being provided with an adhesive layer 22 on the side facing the dressing. A corpuscle of the kind shown in FIG. 3 is intended for a dressing which in the area in which the corpuscles are attached to or are to be attached is non-adhesive, e.g. consists of a woven textile such as gauze or an unwoven textile. The adhesive is not necessarily skin-friendly, but has to be self-adhesive or pressure-sensitive. It might be of the skin barrier type as mentioned hereinbefore with reference to the patent specifications U.S. Pat. No. 3,339,369 and DK Nos. 147,034 and 147,035.

On the side facing the skin the corpuscles 12 may at any rate be provided with a detachable protective cover, not shown, and, if they are separate units, even on the side facing the dressing. They may optionally also be provided with a permanent protective layer on their edges.

On the side facing the wound and/or on their edges the corpuscles may be provided with a barrier layer or a delaying layer in order to regulate seeping of wound secretions and thereby delay the release of the active substance or substances to the wound.

Examples

EXAMPLE 1

To produce a biologically active, discontinuous phase for corpuscles for a dressing material according to the invention, 1.5 g of silver nitrate were dissolved in 1 l of distilled water. 10 g of sodiumcarboxymethyl-cellulose (Na-CMC) were added and stirred in the dark until a homogenous solution was formed, after which the solution was dried overnight in the dark. The silver nitrate-CMC-preparation thus dried was then ground to a medium particle size of 500 $\mu$m.

4.5 g of the powder thus obtained were mixed in the dark with 48.5 g of Na-CMC having a particle size in dry condition of 50 $\mu$m.

To form the passive continuous phase for the same corpuscles, 40.0 g of styrene-butadiene copolymer were melted in a mixer at 130° C. in vacuo. During the melting process and in the dark 10.0 g of liquid paraffin were added as a plasticizer together with the powder mixture mentioned above.

Still hot, the mass was pressed between two inert pieces of siliconized paper to form a sheet having a thickness of 0.1-2 mm, after which the sheet was allowed to cool. After cooling the siliconized paper was removed from one side of the sheet and was substituted by a thin film of a polyvinylethyl adhesive; it was applied as a solution in petroleum ether by a conventional pressing technique.

After evaporation of the solvent the adhesive surface of the sheet thus formed was covered with a silicone protective film after which corpuscles having the desired size and shape were punched from the sheet.

The corpuscles were packed in a lightproof package and may then after removal of the protective film be positioned in a desired pattern and closeness on any kind of bandage by the nursing staff or by the patient himself.

EXAMPLE 2

To produce corpuscles for use in a dressing material according to the invention an active discontinuous phase was prepared by dissolving 10 g of silver lactate in 200 ml of distilled water in the dark and adding, also in the dark, 20 g of Na-CMC to form a homogenous solution which was dried overnight in an oven at 50° C. The dried material was ground and sieved through a vibration sieve having a mesh width of 110 $\mu$m.

Another discontinuous phase was prepared by dissolving 1 g of lactic acid in 250 ml of distilled water and adding 10 g of Na-CMC to form a homogenous solution; the solution was dried in an oven at 50° C. and was then ground to a particle size of 200 μm. The purpose of this phase is to ensure an acid reaction in contact with wound secretion.

A passive discontinuous phase consists of Na-CMC having a particle size of 50 μm.

A further passive discontinuous phase, which is to act as a filler and impart weight to the corpuscles, was produced by grinding 1 g of ZnO of pharmacopoeia grade into a particle size of 200 μm followed by microemcapsulation of the particles in povidone (PVP, polyvinyl pyrrolidone) in a fluid bed to an average particle size of 250 μm.

To form the passive continuous phase 35 g of a vulcanized silicone rubber (forming a foam-like structure) were heated at 130° C. under $N_2$ at a pressure of 1.5 bar in a laboratory mixer, after which 5 g of silicone oil were added as plasticizer. Then 1 g of the micro-encapsulated ZnO-particles, 35 g of the Na-CMC-powder and 5.5 g of the powder containing lactic acid were added. Finally 10 g of the powder containing silver lactate were added.

The mixture was pressed to form a sheet which was cut into corpuscles as described in Example 1, except, however, that a thin film of an acrylic adhesive was used as the adhesive layer.

The corpuscles punched out were adhered to a hydrocolloid dressing in a production plant in such a way that the corpuscles are centrally placed on each single piece of dressing.

EXAMPLE 3

An active discontinuous phase for corpuscles for a dressing material was prepared by dissolving 1.5 g of silver nitrate in 200 ml of 99.5% ethanol. 0.35 g of crystalline NaOH were dissolved therein and the solution was poured on 105 g of dry Na-CMC having a particle size of 50 μm.

Separately 8.8 ml of 1M HCl were dissolved in 100 ml of 99.5% ethanol. The solution was poured over the Na-CMC moistened with the ethanolic silver nitrate solution and stirring was performed in the dark for 3 minutes, after which drying took place overnight at 75° C. in the dark.

As a passive continuous phase there was employed 49 g of polyurethane heated to 140° C. in vacuo in a laboratory mixer, then 15.5 g of dioctylphthalate were added as a plasticizer and 5.0 g of a colourless vaseline. The ingredients were mixed to form a homogeneous matrix after which 34 g of the active discontinuous phase described above were added and mixing continued in the dark for 15 minutes until an even mass was formed.

The mass was pressed in hot condition into sheets in the same way as described in Example 1, and corpuscles were punched, typically having a thickness of 1.0 mm after removal of the protective paper on one side thereof and applying a layer of silicone adhesive for medical use and protection of the adhesive layer with siliconized paper.

EXAMPLE 4

For use as an active discontinuous phase 400 mg of freeze-dried bovine fibronectin were dissolved in 500 ml of distilled water at 37° C. 25 g of hydrolyzed gelatine (to which the fibronectin will bind) were added and mixing took place to obtain a clear solution. The solution was spray-dried to an average particle size of 25 μm.

Na-CMC of a particle size of 50 μm was used as a passive discontinuous phase.

40 g of the same styrene-butadiene block copolymer as used in Example 1 were used as a continuous matrix. It was dissolved in n-hexane, after which 30 g of the Na-CMC powder were admixed while slow stirring. Finally 20 g of the active discontinuous phase described above were added and vigorous stirring continued for 5 minutes.

The semi-solid material thus obtained was poured onto a polyurethane film of a thickness of 25 μm and having a backing of silicone paper. The surface was smoothed out to a thickness of 3 mm. The sheet was placed in an oven having air circulation in order to handle the explosive vapours safely.

After evaporation of the solvent, the film thickness has been reduced. After drying the active discontinuous phase was accumulated above the Na-CMC phase due to the differences in particle size. This favours the release of the active substance, the wound-healing fibronectin, when a dressing provided with such corpuscles is placed on a wound.

When the hexane had evaporated, the open surface was covered with a thin adhesive layer of vinyl ether dissolved in hexane and the layer was covered with siliconized paper.

We claim:

1. A corpuscle for treating wounds in the skin and mucous membranes of the human body, comprising a solid, hydrophobic, water-insoluble, biologically inert, continuous matrix, the matrix being stable at temperatures below about 50° C., the matrix containing at least one hydrophilic discontinuous phase including a biologically active wound care substance, the biologically active substance being dissolved or dispersed in the hydrophilic discontinuous phase or present as a coating thereon.

2. A corpuscle according to claim 1, wherein the corpuscle has a non-adhesive surface on at least the sides intended to face the wound.

3. A corpuscle according to claim 1, further comprising a barrier layer attached to the corpuscle on the side thereof intended to face the wound.

4. A corpuscle according to claim 1, further comprising a layer of adhesive located on the side of the corpuscle which is opposite the side intended to face the wound.

5. A corpuscle according to claim 1, wherein the corpuscle contains a first discontinuous hydrophilic phase containing a first biologically active substance and a second discontinuous hydrophilic phase containing a second biologically active substance.

6. A corpuscle according to claim 1, wherein said biologically active wound care substance comprises a first biologically active substance and a second biologically active substance, the first and second biologically active substances both being present in said at least one discontinous hydrophilic phase.

7. A corpuscle according to claim 5, wherein at least one discontinous phase contains a biologically active substance selected from the group consisting of an antiseptic and an antibiotic, and at least one other discontinous hydrophilic phase contains a biologically active substance of another kind.

8. A corpuscle according to claim 1, further comprising a barrier layer located on the edges of the corpuscle.

9. A dressing material, for treating wounds in the skin and mucous membranes of the human body by successive release of at least one biologically active wound care substance, consisting essentially of:
- a bandage adapted to be attached to the skin or mucous membrane around the wound; and
- at least one corpuscle attached to the side of the bandage intended to face the wound, the corpuscle comprising a solid, hydrophobic, water-insoluble, biologically inert matrix which is stable at temperatures below about 50° C. and at least one hydrophilic discontinous phase containing at least one biologically active substance dispersed or dissolved in, or present as a coating on, particles said of hydrophilic discontinuous phase.

10. A dressing material according to claim 9, wherein the bandage and the at least one corpuscle are attached by an irreversible, adhesive bond.

11. A dressing material according to claim 9, wherein the at least one corpuscles has a non-adhesive surface at least on the side intended to face the wound.

12. A dressing material according to claim 9, wherein the at least one corpuscles contains at least two different hydrophilic phases each containing at least one biologically active substance.

* * * * *